United States Patent
McIntosh et al.

[11] Patent Number: 5,866,682
[45] Date of Patent: Feb. 2, 1999

[54] CONOPEPTIDES AUIA, AUIB AND AUIC

[75] Inventors: J. Michael McIntosh; G. Edward Cartier; Doju Yoshikami; Siqin Luo; Baldomero M. Olivera, all of Salt Lake City, Utah

[73] Assignee: University of Utah Research Foundation, Salt Lake City, Utah

[21] Appl. No.: 857,068

[22] Filed: May 15, 1997

[51] Int. Cl.$^6$ ............................ A61K 38/00; A61K 38/04
[52] U.S. Cl. ...................... 530/326; 530/300; 530/327; 530/857
[58] Field of Search .................... 530/326, 300, 530/327, 857

[56] References Cited

U.S. PATENT DOCUMENTS

| | | | |
|---|---|---|---|
| 4,447,356 | 5/1984 | Olivera et al. | 260/112 R |
| 5,432,155 | 7/1995 | Olivera et al. | 530/324 |
| 5,514,774 | 5/1996 | Olivera et al. | 530/324 |
| 5,633,347 | 5/1997 | Olivera et al. | |

OTHER PUBLICATIONS

Cruz, L.J. et al., "Conus Peptides: Phylogenetic Range of Biological Activity," *Biol. Bull.*, 183:159–164 (Aug., 1992).
International Search Report dated Jul. 30, 1998.
Olivera, B.M. et al. (1985). "Peptide Neurotoxins from Fish–Hunting Cone Snails." *Science* 230:1338–1343.
Olivera, B.M. et al. (1990). "Diversity of Conus Neuropeptides." *Science* 249:257–263.
Ramilo, C.A. et al. (1992). "Novel α–and ω–Conotoxins from *Conus striatus* Venom." *Biochemistry* 31:9919–9926.
Cartier, G.E. et al. (1996). "A New α–Conotoxin Which Targets α3β2 Nicotinic Acetylcholine Receptors." *J. Biol. Chem.* 271:7522–7528.

*Primary Examiner*—Susan A. Loring
*Attorney, Agent, or Firm*—Rothwell, Figg, Ernst & Kurz, P.C.

[57] ABSTRACT

This invention relates to relatively short peptides about 14–17 residues in length, which are naturally available in minute amounts in the venom of the cone snails or analogs to the naturally available peptides, and which include two cyclizing disulfide linkages. More specifically, the present invention is directed to conopeptides having the general formula: Gly-Cys-Cys-Ser-Tyr-$Xaa_1$-$Xaa_1$-Cys-Phe-Ala-Thr-Asn-$Xaa_2$-$Xaa_3$-$Xaa_4$-Cys (SEQ ID NO: 1), wherein $Xaa_1$ is Pro or Hyp (trans-4-hydroxy-Pro), $Xaa_2$ is Ser, Pro or Hyp, $Xaa_3$ is Gly or Asp and $Xaa_4$ is a Tyr or des- $Xaa_4$. The disulfide bridges are between the first and third between the second fourth cysteine residues. The C-terminal end is preferably amidated. The invention further relates to the specific peptides AuIA: Gly-Cys-Cys-Ser-Tyr-Pro-Pro-Cys-Phe-Ala-Thr-Asn-Ser-Asp-Tyr-Cys (SEQ ID NO:2); AuIB: Gly-Cys-Cys-Ser-Tyr-Pro-Pro-Cys-Phe-Ala-Thr-Asn-Pro-Asp-Cys (SEQ ID NO:3); and AuIC: Gly-Cys-Cys-Ser-Tyr-Pro-Pro-Cys-Phe-Ala-Thr-Asn-Ser-Gly-Tyr-Cys (SEQ ID NO:4). The invention also includes pharmaceutically acceptable salts of the conopeptides.

12 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 16 amino acids
      ( B ) TYPE: amino acid
      ( C ) STRANDEDNESS:
      ( D ) TOPOLOGY: linear ( i i ) MOLECULE TYPE: protein ( v i ) ORIGINAL SOURCE:
      ( A ) ORGANISM: Conus aulicus ( i x ) FEATURE:
      ( A ) NAME/KEY: Disulfide-bond
      ( B ) LOCATION: 2..8

( i x ) FEATURE:
      ( A ) NAME/KEY: Disulfide-bond
      ( B ) LOCATION: 3..16

( i x ) FEATURE:
      ( A ) NAME/KEY: Peptide
      ( B ) LOCATION: 6..7
      ( D ) OTHER INFORMATION: /note= "Xaa at residues 6 or 7 may
         be Pro or Hyp"

( i x ) FEATURE:
      ( A ) NAME/KEY: Peptide
      ( B ) LOCATION: 13..14
      ( D ) OTHER INFORMATION: /note= "Xaa at residue 13 may be
         Ser, Pro or Hyp"

( i x ) FEATURE:
      ( A ) NAME/KEY: Peptide
      ( B ) LOCATION: 14..15
      ( D ) OTHER INFORMATION: /note= "Xaa at residue 14 may be
         Gly or Asp"

( i x ) FEATURE:
      ( A ) NAME/KEY: Peptide
      ( B ) LOCATION: 15..16
      ( D ) OTHER INFORMATION: /note= "Xaa at residue 15 may be
         Tyr or des- Xaa"

( x i ) SEQUENCE DESCRIPTION: SEQ ID NO:1:

```
Gly  Cys  Cys  Ser  Tyr  Xaa  Xaa  Cys  Phe  Ala  Thr  Asn  Xaa  Xaa  Xaa  Cys
1                  5                        10                      15
```

( 2 ) INFORMATION FOR SEQ ID NO:2:

( i ) SEQUENCE CHARACTERISTICS:
      ( A ) LENGTH: 16 amino acids
      ( B ) TYPE: amino acid
      ( C ) STRANDEDNESS:
      ( D ) TOPOLOGY: linear ( i i ) MOLECULE TYPE: protein ( v i ) ORIGINAL SOURCE:
      ( A ) ORGANISM: Conus aulicus ( i x ) FEATURE:
      ( A ) NAME/KEY: Disulfide-bond
      ( B ) LOCATION: 2..8

( i x ) FEATURE:

(A) NAME/KEY: Disulfide-bond
            (B) LOCATION: 3..16

(xi) SEQUENCE DESCRIPTION: SEQ ID NO:2:

Gly Cys Cys Ser Tyr Pro Pro Cys Phe Ala Thr Asn Ser Asp Tyr Cys
1               5                   10                  15

(2) INFORMATION FOR SEQ ID NO:3:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: protein (vi) ORIGINAL SOURCE:
            (A) ORGANISM: Conus aulicus (ix) FEATURE:
            (A) NAME/KEY: Disulfide-bond
            (B) LOCATION: 2..8

(ix) FEATURE:
            (A) NAME/KEY: Disulfide-bond
            (B) LOCATION: 3..15

(xi) SEQUENCE DESCRIPTION: SEQ ID NO:3:

Gly Cys Cys Ser Tyr Pro Pro Cys Phe Ala Thr Asn Pro Asp Cys
1               5                   10                  15

(2) INFORMATION FOR SEQ ID NO:4:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: protein (vi) ORIGINAL SOURCE:
            (A) ORGANISM: Conus aulicus (ix) FEATURE:
            (A) NAME/KEY: Disulfide-bond
            (B) LOCATION: 2..8

(ix) FEATURE:
            (A) NAME/KEY: Disulfide-bond
            (B) LOCATION: 3..16

(xi) SEQUENCE DESCRIPTION: SEQ ID NO:4:

Gly Cys Cys Ser Tyr Pro Pro Cys Phe Ala Thr Asn Ser Gly Tyr Cys
1               5                   10                  15

CONOPEPTIDES AUIA, AUIB AND AUIC

This invention was made with Government support under Grant Nos. GM48677 and MH53631 awarded by the National Institutes of Health, Bethesda, M. The United States Government has certain rights in the invention.

BACKGROUND OF THE INVENTION

This invention relates to relatively short peptides about 14–17 residues in length, which are naturally available in minute amounts in the venom of the cone snails or analogs to the naturally available peptides, and which include two cyclizing disulfide linkages.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Mollusks of the genus Conus produce a venom that enables them to carry out their unique predatory lifestyle. Prey are immobilized by the venom that is injected by means of a highly specialized venom apparatus, a disposable hollow tooth that functions both in the manner of a harpoon and a hypodermic needle.

Few interactions between organisms are more striking than those between a venomous animal and its envenomated victim. Venom may be used as a primary weapon to capture prey or as a defense mechanism. Many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used, however, every Conus species uses fundamentally the same basic pattern of envenomation.

Several peptides isolated from Conus venoms have been characterized. These include the $\alpha$-, $\beta$- and $\omega$-conotoxins which target nicotinic acetylcholine receptors, muscle sodium channels, and neuronal calcium channels, respectively (Olivera et al., 1985). Conopressins, which are vasopressin analogs, have also been identified (Cruz et al. 1987). In addition, peptides named conantokins have been isolated from Conus geographus and Conus tulipa (Mena et al., 1990; Haack et al., 1990). These peptides have unusual age-dependent physiological effects: they induce a sleep-like state in mice younger than two weeks and hyperactive behavior in mice older than 3 weeks (Haack et al., 1990). Recently, peptides named contryphans containing D-tryptophan residues have been isolated from Conus radiatus (U.S. Ser. No. 60/030,722), and bromo-tryptophan conopeptides have been isolated from Conus imperialis and Conus radiatus (U.S. Ser. No. 08/785,534).

Neuronal nicotinic acetylcholine receptors (nAChRs) are believed to be heteropentameric ion channel complexes generally requiring at least two different subunits (an $\alpha$ and a $\beta$). Molecular data indicate that in the mammalian central nervous system there exists a large number of different nAChR subunits. To date, seven different $\alpha$ subunits ($\alpha2-\alpha7$, $\alpha9$) and three different $\beta$ subunits ($\beta2-\beta4$) have been defined by cloning. The $\alpha3\beta4$ nAChR subtype and the $\alpha3\beta2$ nAChR subtype are each present in the autonomic nervous system and in the central nervous system. The $\alpha7$ nAChR subtype is also present in the autonomic nervous system.

While postsynaptic nAChRs have been recognized for some time, more recent data have demonstrated the presence of presynaptic neuronal nAChRs. Agonist stimulation of presynaptic nAChRs induces neurotransmitter release. Nicotinic agonists have been shown to elicit the release of several different neurotransmitters, including dopamine from striatum and frontal cortex (El-Bizri and Clarke, 1994; Grady et al., 1992; Rapier et al., 1988); norepinephrine from hippocampus (Clarke and Reuben, 1996; Rowell and Winkler, 1984; Sacaan et al., 1995; Wilkie et al., 1993); glutamate from cortex, medial habenula nucleus and hippocampus (McGehee and Role, 1995; Vidal and Changeux, 1993; Gray et al., 1996); GABA from interpeduncular nucleus (Mulle et al., 1991) and acetylcholine for cortex and hippocampus (Lapchak et al., 1989; Rowell and Winkler, 1984).

In addition, it appears that distinct subtypes of presynaptic nAChRs regulate the release of different neurotransmitters. For example, nicotine-stimulated glutamate and acetylcholine release are blocked by $\alpha$-bungarotoxin suggesting that these nAChRs include an $\alpha7$ subunit (McGehee and Role, 1995). In contrast, nicotine-stimulated dopamine release is not blocked by $\alpha$-bungarotoxin (Grady et al., 1992). Furthermore, the nAChRs modulating norepinephrine release pharmacologically differ from those modulating the release of glutamate, acetylcholine or dopamine (Clarke and Reuben, 1996; Sacaan et al., 1995).

The possibility of selectively modulating the presynaptic release of specific neurotransmitters and the possibility of selectively targeting specific nAChRs has significant therapeutic applications. One example of a therapeutic application is tobacco addiction. Studies of nicotine self-administration in animal models suggest that block of nAChRs decreases the reinforcing properties of nicotine. Examples of therapeutic applications resulting from selectively targeting the nAChRs of the autonomic nervous system are the treatment of cardiovascular disorders, gastric mobility disorders and urinary incontinence.

It is desired to identify additional compounds which target different nAChR subtypes as well as the nAChR subtypes of the autonomic nervous system and the central nervous system. It is further desired to identify compounds which are useful as cardiovascular agents, gastric motility agents, urinary incontinence agents and anti-smoking agents.

SUMMARY OF THE INVENTION

This invention relates to relatively short peptides about 14–17 residues in length, which are naturally available in minute amounts in the venom of the cone snails or analogs to the naturally available peptides, and which include two cyclizing disulfide linkages. More specifically, the present invention is directed to conopeptides having the general formula: Gly-Cys-Cys-Ser-Tyr-Xaa$_1$-Xaa$_1$-Cys-Phe-Ala-Thr-Asn-Xaa$_2$-Xaa$_3$-Xaa$_4$-Cys (SEQ ID NO:1), wherein Xaa$_1$ is Pro or Hyp (trans-4-hydroxy-Pro), Xaa$_2$ is Ser, Pro or Hyp, Xaa$_3$ is Gly or Asp and Xaa$_4$ is a Tyr or des-Xaa$_4$. The disulfide bridges are between the first and third cysteine residues and between the second and fourth cysteine residues. The C-terminal end is preferably amidated. The invention also includes pharmaceutically acceptable salts of the conopeptides. These conopeptides are useful as cardiovascular agents, gastric motility agents, urinary incontinence agents and anti-smoking agents.

The invention further relates to the specific peptides: AuIA: Gly-Cys-Cys-Ser-Tyr-Pro-Pro-Cys-Phe-Ala-Thr-Asn-Ser-Asp-Tyr-Cys (SEQ ID NO:2); AuIB: Gly-Cys-Cys-Ser-Tyr-Pro-Pro-Cys-Phe-Ala-Thr-Asn-Pro-Asp-Cys (SEQ ID NO:3); and AuIC: Gly-Cys-Cys-Ser-Tyr-Pro-Pro-Cys-Phe-Ala-Thr-Asn-Ser-Gly-Tyr-Cys (SEQ ID NO:4).

DETAILED DESCRIPTION OF THE PREFERRED EMBODIMFNT

This invention relates to relatively short peptides about 14–17 residues in length, which are naturally available in minute amounts in the venom of the cone snails or analogs to the naturally available peptides, and which include two cyclizing disulfide linkages. More specifically, the present invention is directed to conopeptides having the general formula: Gly-Cys-Cys-Ser-Tyr-$Xaa_1$-$Xaa_1$-Cys-Phe-Ala-Thr-Asn-$Xaa_2$-$Xaa_3$-$Xaa_4$-Cys (SEQ ID NO: 1), wherein $Xaa_1$ is Pro or Hyp (trans-4-hydroxy-Pro), $Xaa_2$ is Ser, Pro or Hyp, $Xaa_3$ is Gly or Asp and $Xaa_4$ is a Tyr or des-$Xaa_4$. The disulfide bridges are between the first and third cysteine residues and between the second and fourth cysteine residues. The C-terminal end is preferably amidated. The invention also includes pharmaceutically acceptable salts of the conopeptides.

The invention further relates to the specific peptides: AuIA: Gly-Cys-Cys-Ser-Tyr-Pro-Pro-Cys-Phe-Ala-Thr-Asn-Ser-Asp-Tyr-Cys (SEQ ID NO:2); AuIB: Gly-Cys-Cys-Ser-Tyr-Pro-Pro-Cys-Phe-Ala-Thr-Asn-Pro-Asp-Cys (SEQ ID NO:3); and AuIC: Gly-Cys-Cys-Ser-Tyr-Pro-Pro-Cys-Phe-Ala-Thr-Asn-Ser-Gly-Tyr-Cys (SEQ ID NO:4).

The conopeptides of the present invention are active on the $\alpha 3\beta 4$ subtype of nAChRs which are present in the autonomic and central nervous systems. Thus, they are useful as cardiovascular agents, gastric motility agents, urinary incontinence agents and anti-smoking agents.

These peptides are sufficiently small to be chemically synthesized. General chemical syntheses for preparing the foregoing conopeptides peptides are described hereinafter, along with specific chemical synthesis of conopeptides and indications of biological activities of these synthetic products. Various ones of these conopeptides can also be obtained by isolation and purification from specific *Conus* species using the technique described in U.S. Pat. No. 4,447,356 (Olivera et al., 1984), the disclosure of which is incorporated herein by reference.

Although the conopeptides of the present invention can be obtained by purification from cone snails, because the amounts of conopeptides obtainable from individual snails are very small, the desired substantially pure conopeptides are best practically obtained in commercially valuable amounts by chemical synthesis using solid-phase strategy. For example, the yield from a single cone snail may be about 10 micrograms or less of conopeptide. By "substantially pure" is meant that the peptide is present in the substantial absence of other biological molecules of the same type; it is preferably present in an amount of at least about 85% purity and preferably at least about 95% purity. Chemical synthesis of biologically active conopeptides depends of course upon correct determination of the amino acid sequence. Thus, the conopeptides of the present invention may be isolated, synthesized and/or substantially pure.

The conopeptides can also be produced by recombinant DNA techniques well known in the art. Such techniques are described by Sambrook et al. (1979). The peptides produced in this manner are isolated, reduced if necessary, and oxidized to form the correct disulfide bonds, if present in the final molecule.

One method of forming disulfide bonds in the conopeptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conopeptide molecule. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. 4,105,603 (Vale et al., 1978). The fragment condensation method of synthesis is exemplified in U.S. Pat. 3,972, 859 (1976). Other available syntheses are exemplified by U.S. Pat. Nos. 3,842,067 (1974) and 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH BHA resin support, or —NH—MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder and Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder and Lubke (1965) and Kapoor (1970).

Each protected amino acid or amino acid sequence is introduced into the solid-phase reactor in about a twofold or more excess, and the coupling may be carried out in a medium of dimethylformamide (DMF):CH$_2$Cl$_2$ (1:1) or in DMF or CH$_2$Cl$_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The present α-conotoxins block α3β4 nAChRs expressed in Xenopus oocytes. The present α-conotoxins also block other nAChR subunit combinations but with much lower affinities. At low submicromolar concentrations, e.g., 0.3–1.0 μM, the present α-conotoxins block essentially only α3β4 receptors. It is know that α-conotoxin MII blocks native α3β2-containing nAChRs and α3β4 conataining nAChRs ( U.S. Pat. No. 5,780,433 incorporated herein by reference).

A particular advantage of α-conotoxin antagonists is their ability to discriminate between nonsymmetrical ligand binding interfaces present on the receptor. The best-studied example is α-conotoxin MI binding to the muscle nicotinic receptor. In mouse muscle, α-conotoxin MI displays a four order-of-magnitude selectivity for the α1/δ vs. the α1/γ binding site (Sine and Claudio, 1991). Nevertheless, α-conotoxin MI functionally blocks the muscle receptor with affinity comparable to its affinity for the α1/δ binding site, indicating that only one toxin molecule is required to prevent channel activation (Martinez et al., 1995). It was also recently demonstrated that α-conotoxin MII has two binding sites on α3β2 and α3β4 receptors expressed in Xenopus oocytes and only one toxin molecule is required to block function (Cartier et al., 1996b). α-Conotoxin MII discriminates between the α3β2 and α3β4 interface by four orders-of-magnitude (see Ser. No. 08/761,674). Thus, α-conotoxin MII has the ability to potently block any receptor containing an α3β2 subunit interface regardless of what other α and β subunits may be present in the receptor complex. α-Conotoxin MII's potency at such receptors would still be high. Similarly, it has now been found that the α-conotoxins of the present invention, including AuIA, AuIB and AuIC, have the ability to discriminate between the α3β4 and α3β2 interface. Consequently, these α-conotoxins have the ability to potently block any receptor containing an α3β4 subunit interface regardless of what other α and β subunits may be present in the receptor complex. The present α-conotoxins' potency at such receptors would still be high.

Pharmaceutical compositions containing a compound of the present invention as the active ingredient can be prepared according to conventional pharmaceutical compounding techniques. See, for example, *Remington's Pharmaceutical Sciences,* 17th Ed. (1985, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral. The compositions may further contain antioxidizing agents, stabilizing agents, preservatives and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The conopeptides are administered in an amount sufficient to antagonize the α3β4 nAChRs. The dosage range at which the conopeptides exhibit this antagonistic effect can vary widely depending upon the particular condition, e.g., cardiovascular disorders, gastric motility disorders, urinary incontinence or nicotine addiction, being treated, the severity of the patient's condition, the patient, the specific conotoxin being administered, the route of administration and the presence of other underlying disease states within the patient. Typically the conopeptides of the present invention exhibit their therapeutic effect at a dosage range from about 0.05 mg/kg to about 250 mg/kg, and preferably from about 0.1 mg/kg to about 100 mg/kg of the active ingredient. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved.

EXAMPLES

The present invention is described by reference to the following Examples, which are offered by way of illustration and are not intended to limit the invention in any manner. Standard techniques well known in the art or the techniques specifically described below were utilized.

EXAMPLE 1

Purification of α-Conotoxins From *Conus aulicus*

Crude venom was extracted from venom ducts (Cruz et al., 1976), and the components were purified as previously described (Cartier et al., 1996a). The crude extract from venom ducts was purified by reverse phase liquid chromatography (RPLC) using a Vydac $C_{18}$ semi-preparative column (10×250 mm) and elution with a linear gradient of acetonitrile in 0.1% TFA. Further purification of bioactive peaks was done on a Vydac $C_{18}$ analytical column (4.6×220 mm) eluted with a gradient of acetonitrile in 0.1% TFA. The effluents were monitored at 220 nm. Peaks were collected, and aliquots were assayed for activity. Activity was monitored by assessing block of α3β4 nAChRs expressed in Xenopus oocytes.

EXAMPLE 2

Sequence Determination of α-Conotoxins From *Conus aulicus*

The amino acid sequence of the purified peptides were determined by standard methods. The purified peptides were reduced and alkylated prior to sequencing by automated Edman degradation on an Applied Biosystems 477A Protein Sequencer with a 120A Analyzer (DNA/Peptide Facility, University of Utah) (Martinez et al., 1995; Shon et al., 1994). The results of the amino acid sequencing runs revealed three peptides having the sequences:

AuIA: Gly-Cys-Cys-Ser-Tyr-Pro-Pro-Cys-Phe-Ala-Thr-Asn-Ser-Asp-Tyr-Cys (SEQ ID NO:2); AuIB: Gly-Cys-Cys-Ser-Tyr-Pro-Pro-Cys-Phe-Ala-Thr-Asn-Pro-Asp-Cys (SEQ ID NO:3); and AuIC: Gly-Cys-Cys-Ser-Tyr-Pro-Pro-Cys-Phe-Ala-Thr-Asn-Ser-Gly-Tyr-Cys (SEQ ID NO:4).

EXAMPLE 3

Chemical Synthesis of α-Conotoxins From *Conus aulicus*

The synthesis of AuIA, AuIB and AuIC conopeptides was separately performed using conventional protection chemistry as described by Cartier et al., 1996a. Briefly, the linear chains were built on Rink amide resin by Fmoc procedures with 2-(1 H-benzotriol-1-yl)-1,1,3,3,-tetramethyluronium tetrafluoroborated coupling using an ABI model 430A peptide sythesizer with amino acid derivatives purchased from Bachem (Torrence Calif.). Orthogonal protection was used on cysteines: $Cys^3$ and $Cys^{16}$ were protected as the stable Cys(S-acetamidomethyl), while $Cys^2$ and $Cys^8$ were protected as the acid-labile Cys(S-trityl). After removal of the terminal Fmoc protecting group and cleavage of the peptides from the resins, the released peptides were precipitated by filtering the reaction mixture into −10° C. methyl t-butyl ether, which removed the protecting groups except on $Cys^3$ and $Cys^{16}$. The peptides were dissolved in 0.1% TFA and 60% aceonitrile and purified by RPLC on a Vydac $C_{18}$ prepartive column (22×250 mm) and eluted at a flow rate of 20 mL/min with a gradient of acetonitrile in 0.1% TFA.

The disulfide bridges in the three conopeptides were formed as described in Cartier et al. (1996a). Briefly, the disulfide bridges between $Cys^2$ and $Cys^8$ were formed by air oxidation which was judged to be complete by analytical RPLC. The monocyclic peptides were purified by RPLC on a Vydac $C_{18}$ prepartive column (22×250 mm) and eluted with a gradient of acetonitrile in 0.1% TFA. Removal of S-acetamidomethyl groups and closure of the disulfide bridge between $Cys^3$ and $Cys^{16}$ was carried out simultaneously be iodine oxidation. The cyclic peptides were purified by RPLC on a Vydac $C_{18}$ prepartive column (22×250 mm) and eluted with a gradient of acetonitrile in 0.1% TFA.

EXAMPLE 4

Biological Activity of α-Conotoxins From *Conus aulicus*

Each of the AuIA, AuIB and AuIC conopeptides were tested for activity on neuronal nAChRs in *Xenopus laevis* oocytes containing different subtypes of nAChRs as described by Cartier et al. (1996a). Briefly, oocytes were injected with RNA encoding the various α and β subunits of rat nAChRs and incubated at 25° C. for 1–9 days prior to use. Electrophysiological currents were measured using conventional techniques, such as described in Cartier et al. (1996a). Measurements were made for oocytes perfused with acetylcholine as controls and for oocytes incubated with 1 μM of either AuIA conopeptide, AuIB conopeptide or AuIC conopeptide followed by perfusion with acetylcholine. Each of these conopeptides was active on neuronal nAChRs with a preference for nAChRs of the α3β4 subtype.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Bodansky et al. (1966). *Chem. Ind.* 38:1597–98.
Cartier, G. E. et al. (1996a). *J Biol. Chem.* 271:7522–7528.
Cartier, G. E. et al. (1996b). *Soc. Neurosci. Abst.* 22:268.
Clarke, P. B. S. and Reuben, M. (1996). *Br. J Pharmacol.* 111:695–702.
Cruz, L. J. at al. (1976). *Verliger* 18:302–308.
Cruz, L. J. et al. (1987). *Conus geographus* toxins that discriminate between neuronal and muscle sodium channels. *J. Biol. Chem.* 260:9280–9288.
El-Bizri, H. and Clarke, P. B. S. (1994). *Br. J Pharmacol.* 111:406–413.
Grady, S. et al. (1992). *J. Neurochem.* 59:848–856.
Gray, R. et al. (1996). *J. Neurochem.* 59:848–856.
Haack, J. A. et al. (1990). Contryphan-T: a gamma-carboxyglutamate containing peptide with N-methyl-d-aspartate antagonist activity. *J Biol. Chem.* 265:6025–6029.
Horiki, K. et al. (1978). *Chemistry Letters* 165–68.
Kaiser et al. (1970). *Anal. Biochem.* 34:595.
Kapoor (1970). *J. Pharm. Sci.* 59:1–27.
Kornreich, W. D. et al. (1986). U.S. Pat. No. 4,569,967.
Lapchak, P. A. et al. (1989). *J. Neurochem.* 52:483–491.
Martinez, J. S. et al. (1995). *Biochem.* 34:14519–14526.
McGehee, D. S. and Role, L. W. (1995). *Annu. Rev. Physiol.* 57:521–546.
Mena, E. E. et al. (1990). Contryphan-G: a novel peptide antagonist to the N-methyl-D-aspartic acid (NMDA) receptor. *Neurosci. Lett.* 118:241–244.
*Methoden der Organischen Chemie (Houben-Weyl): Synthese von Peptiden*, E. Wunsch (Ed.), Georg Thieme Verlag, Stuttgart, Ger. (1974).
Mulle, C. et al. (1991). *J. Neurosci.* 11:2588–2597.
Nishiuchi, Y. et al. (1993). Synthesis of gamma-carboxyglutamic acid-containing peptides by the Boc strategy. *Int. J. Pept. Protein Res.* 42:533–538.
Olivera, B. M. et al. (1984). U.S. Pat. 4,447,356.
Olivera, B. M. et al. (1985). Peptide neurotoxins from fish-hunting cone snails. *Science* 230:1338–1343.
Rapier, C. et al. (1988). *J. Neurochem.* 50:1123–1130.
*Remington's Pharmaceutical Sciences*, 17th Ed., Mack Publishing Co., Easton, Pa. (1985).
Rivier, J. R. et al. (1978). *Biopolymers* 17:1927–38.
Rivier, J. R. et al. (1987). Total synthesis and further characterization of the gamma-carboxyglutamate-containing 'sleeper' peptide from *Conus geographus*. *Biochem.* 26:8508–8512.
Rowell, P. P. and Winkler, D. L. (1984). *J. Neurochem.* 43:1593–1598.
Sacaan, A. I. et al. (1995). *J. Pharmacol. Exp. Therapeutics* 274:224–230.
Sambrook, J. et al. (1979). *Molecular Cloning. A Laboratory Manual*, 2nd Ed., Cold Spring Harbor Laboratory, Cold Spring Harbor, N.Y.
Schroder & Lubke (1965). *The Peptides* 1:72–75, Academic Press, NY.
Shon, K. -J. et al. (1994). *Biochemistry* 33:11420–11425.
Sine, S. M. and Claudio, T. (1991). *J. Biol. Chem.* 266:19369–19377.
Stewart and Young, *Solid-Phase Peptide Synthesis*, Freeman & Co., San Francisco, Calif. (1969).
Vale et al. (1978). U.S. Pat. No. 4,105,603.
Vidal, C. and Changeux, J. -P. (1993). *Neuroscience* 56:23–32.
Wilkie, G. I. et al. (1993). *Biochem. Soc. Trans.* 21:429–431.
Zhou L. M., et al. (1996a). Synthetic Analogues of Contryphan-G: NMDA Antagonists Acting Through a Novel Polyamine-Coupled Site. *J. Neurochem.* 66:620–628.

U.S. Pat. No. 3,972,859 (1976).
U.S. Pat. No. 3,842,067 (1974).

U.S. Pat. No. 3,862,925 (1975).
PCT Published Application WO 96/11698

What is claimed is:

1. A substantially pure conopeptide having the general formula: Gly-Cys-Cys-Ser-Tyr-$Xaa_1$-$Xaa_1$-Cys-Phe-Ala-Thr-Asn-$Xaa_2$-$Xaa_3$-$Xaa_4$-Cys (SEQ ID NO:1), wherein $Xaa_1$ is Pro or Hyp, $Xaa_2$ is Ser, Pro or Hyp, $Xaa_3$ is Gly or Asp and $Xaa_4$ is a Tyr or des-$Xaa_4$.

2. The conopeptide of claim 1 wherein the C-terminus is amidated.

3. The conopeptide of claim 1 wherein $Xaa_1$ is Pro.
4. The conopeptide of claim 1 wherein $Xaa_2$ is Pro.
5. The conopeptide of claim 1 wherein $Xaa_2$ is Ser.
6. The conopeptide of claim 1 wherein $Xaa_3$ is Gly.
7. The conopeptide of claim 1 wherein $Xaa_3$ is Asp.

8. The conopeptide of claim 1 wherein $Xaa_4$ is Tyr.
9. The conopeptide of claim 1 wherein $Xaa_4$ is des-$Xaa_4$.
10. The conopeptide of claim I having the formula Gly-Cys-Cys-Ser-Tyr-Pro-Pro-Cys-Phe-Ala-Thr-Asn-Ser-Asp-Tyr-Cys (SEQ ID NO:2).
11. The conopeptide of claim 1 having the formula Gly-Cys-Cys-Ser-Tyr-Pro-Pro-Cys-Phe-Ala-Thr-Asn-Pro-Asp-Cys (SEQ ID NO:3).
12. The conopeptide of claim 1 having the formula Gly-Cys-Cys-Ser-Tyr-Pro-Pro-Cys-Phe-Ala-Thr-Asn-Ser-Gly-Tyr-Cys (SEQ ID NO:4).

* * * * *